US006735469B2

(12) United States Patent
Lee et al.

(10) Patent No.: US 6,735,469 B2
(45) Date of Patent: May 11, 2004

(54) APPARATUS AND METHOD FOR OBTAINING DATA FOR DIAGNOSING CONDITION OF LIVING BODY USING UHF SIGNAL

(75) Inventors: Sang-min Lee, Seoul (KR); Wan-taek Han, Suwon (KR); Mickail Anatolievich Krevsky, Nizhny Novgorod (RU); Yury Ivanovich Kashurinov, Nizhny Novgorod (RU); Ekaterina Sergeevna Zinina, Nizhny Novgorod (RU); Eugebi Yurievich Marov, Kstovo (RU); Aleksey Mikhailovich Ovechkin, Nizhny Novgorod (RU); Yury Alekzandrovich Tkachenko, Nizhny Novgorod (RU)

(73) Assignee: Samsung Electronics Co., Ltd., Kyungki-do (KR)

( * ) Notice: Subject to any disclaimer, the term of this patent is extended or adjusted under 35 U.S.C. 154(b) by 102 days.

(21) Appl. No.: 10/029,232

(22) Filed: Dec. 28, 2001

(65) Prior Publication Data

US 2002/156358 A1 Oct. 24, 2002

(30) Foreign Application Priority Data

Dec. 28, 2000 (RU) .............................. 2000132892

(51) Int. Cl.$^7$ ................................................ A61H 39/02
(52) U.S. Cl. ........................................................ 600/548
(58) Field of Search ............................ 600/548, 372; 128/907; 607/116, 1, 2, 46

(56) References Cited

U.S. PATENT DOCUMENTS 4,408,617 A * 10/1983 Auguste ................... 600/548

FOREIGN PATENT DOCUMENTS

FR 2 473 882 10/1983
RU 2143840 * 1/2000

OTHER PUBLICATIONS

Samosjuk, I.Z., et al., "Untraditional Methods of Diagnostic and Therapy", Zdalovya (Publisher), Kiev, pp. 174–187, (1994) [English language translation not presently available.].

* cited by examiner

Primary Examiner—George Manuel
Assistant Examiner—Ruby Jain
(74) Attorney, Agent, or Firm—Lee & Sterba, P.C.

(57) ABSTRACT

An apparatus and method for obtaining data for diagnosing the condition of a living body without harming living tissue using an ultrahigh frequency (UHF) signal includes a signal transmitter, a signal receiver, and a signal processor. Signal transmitter generates a UHF signal and radiates the UHF signal at a first of two acupuncture points of a living body. The signal receiver receives a UHF signal emitted from a second acupuncture point, detects and outputs the magnitude of the received UHF signal. The signal processor compares the detected magnitude of the received UHF signal with a magnitude of the UHF signal generated by the signal transmitter, calculates from the result of comparing and recording a conductivity of each of the acupuncture sections when the UHF signal passes through the corresponding acupuncture section, calculates at least one of a first variation, which indicates a degree of variation in conductivities of the acupuncture sections, and a second variation, which indicates a degree of variation in conductivities for a plurality of channels, using at least two recorded conductivities of the respective acupuncture sections, and outputs the result of calculation as data for diagnosing the condition of the living body.

42 Claims, 12 Drawing Sheets

APPARATUS AND METHOD FOR OBTAINING DATA FOR DIAGNOSING CONDITION OF LIVING BODY USING UHF SIGNAL

BACKGROUND OF THE INVENTION

1. Field of the Invention

The present invention relates to data for diagnosing the condition of a living body. More particularly, the present invention relates to an apparatus and method for obtaining data for diagnosing the condition of a living body using an ultrahigh frequency (UHF) signal.

2. Description of the Related Art

Generally in medicine, and more particularly in diagnosing the health condition of a human body using an electromagnetic field having a power that does not generate heat, a method of analyzing the state of a channel composed of acupuncture points can be used. In this method, a UHF signal is radiated at the skin of a human body and obtains data for diagnosing the state of each organ in the human body, or the functional state of an organ corresponding to a channel, using UHF signals that have been reflected from and transmitted through the skin.

A conventional method of analyzing the state of a channel is disclosed on pages 174–187 of a book written by I. Z. Samosjuk, V. P. Lysenjuk, and J. P. Limansky, entitled "Untraditional Methods of Diagnostic and Therapy", and published by Zdalovya in Kiev in 1994. In the disclosed method, an electrical signal is radiated at a human body, a signal detected from the human body is processed, and an analysis method (electro-puncture diagnosis) involving radiating an electron wave at a human body is used for analyzing the state of points on the body suitable for acupuncture based on the state of 12 channels. According to this method, electro-skin resistance or impedance (ESR) is obtained with respect to each selected point. Also, an average ESR with respect to a plurality of points is obtained, and the deviation between the average and the ESR of each channel is obtained, so the state of the points are estimated from the deviation. However, in such a conventional method, precise measurement of the ESR is difficult because current is applied to a human body while ESR is measured. The accuracy of ESR may decrease according to the state of a connection between an electrode and skin, moistness of the skin, or the method used to stick the electrode to the skin, specifically, an angle between the electrode and the skin can reduce accuracy of ESR measurements. Accordingly, this method cannot precisely analyze the state of a channel because ESR cannot be precisely measured.

Another conventional method of analyzing the state of a channel using the radiation of a UHF signal having a power that does not generate heat is disclosed in Russian Federation Patent No. 2143840 published on Jan. 10, 2000. In this conventional method, a UHF signal having fixed amplitudes at different frequencies in a frequency band ranging from 300 MHz to 600 MHz is radiated at an acupuncture point of a channel through a transmitting antenna to analyze the state of each channel. For this, an output signal from another point of the aforementioned channel is received through a receiving antenna, and the maximum conductivity (determined by the ratio of a received signal to a radiated signal) of the section between the points in the above frequency band is obtained. With such a process, maximum conductivities for 12 channels are sequentially obtained. Next, the average of the conductivities for the 12 channels is obtained. The conductivity deviation value for each channel is obtained on the basis of the average of the conductivities and is used as a diagnostic index. However, such a conventional method does not provide sufficient data for analyzing the state of a channel, so it is difficult to diagnose a chronic disease using this method.

A conventional apparatus for analyzing the state of a living body at points suitable for acupuncture to diagnose the condition of a human body and treat the human body is disclosed in France Patent Application No. 2473882 filed in 1981. This conventional apparatus includes a probe generator for transmitting an electrical signal of a ramp function type, a charging circuit, and a control device. Such a conventional apparatus simply detects the positions of points on a patient's body and does not provide information about the state of points, which characterizes the energy state of a channel. Moreover, as described above, since ESR changes in a complicated manner according to pressure or an angle at which a probe penetrates skin, during diagnosis using an electrical signal such a conventional apparatus cannot precisely analyze the state of points.

Another conventional apparatus for analyzing the state of a channel to diagnose the condition of and treat a human body by feeding a UHF signal to an acupuncture point is disclosed in the above-mentioned Russian Federation Patent. This conventional apparatus includes a charging circuit, a control circuit, a UHF signal generator connected to the control circuit, a transmitting antenna, and a receiving antenna. Here, the receiving antenna is connected to a UHF signal detector, and the UHF signal detector is connected to a channel selector switch through a power amplifier. A first output terminal of the channel selector switch is connected to an input terminal of an indicator that indicates the energy state of a channel. A second output terminal of the channel selector switch is connected to an input terminal of an averaging block which stores data about the energy state of channels and averages the stored data. The averaging block is connected to an input terminal of a deviation block that determines a deviation value on the basis of the average. The deviation block is connected to an indicator, which indicates the deviation value. However, such a conventional apparatus radiates a UHF signal having a power of several milliwatts (mW) at a human body, which may be harmful to the human body. Furthermore, a several milliwatt UHF signal increases the probability of erroneously measuring conductivity. In addition, since an antenna of a transmitter is vulnerable to noise, the sensitivity of a receiver may be decreased. Moreover, such a conventional apparatus cannot obtain sufficient data about the state of a channel, so the precision of analysis of the state of an organ corresponding to the channel decreases.

SUMMARY OF THE INVENTION

To solve the above-described problems, it is a first feature of a preferred embodiment of the present invention to provide an apparatus for obtaining enough data to diagnose the condition of a living body using radiation of an ultrahigh frequency (UHF) signal of a low level directed into the living body.

It is a second feature of a preferred embodiment of the present invention to provide a method of obtaining enough data to diagnose the condition of a living body using radiation of a UHF signal of a low level directed into the living body.

To achieve the first feature of an embodiment of the present invention, there is provided an apparatus for obtaining data for diagnosing the condition of a living body using a UHF signal. The apparatus includes a signal transmitter for generating a UHF signal having a frequency in an ultrahigh frequency band and radiating the generated UHF signal at a first point which is one of two acupuncture points which exist on each of at least two acupuncture sections of a living body. The apparatus further includes a signal receiver for receiving a UHF signal emitted from a second point, which is the other one of the two acupuncture points. The signal receiver also detects the magnitude of the received UHF signal and outputs the detected magnitude. The apparatus also includes a signal processor for comparing the detected magnitude of the received UHF signal with a magnitude of the UHF signal generated by the signal transmitter. From the result of comparison, the signal processor also calculates and records a conductivity of each of the acupuncture sections when the UHF signal passes through the corresponding acupuncture section, calculating at least one of a first variation, which indicates a degree of variation in conductivities of the acupuncture sections, and a second variation, which indicates a degree of variation in conductivities for a plurality of channels, using at least two recorded conductivities of the respective acupuncture sections, and outputting the result of calculation as data for diagnosing the condition of the living body.

To achieve the second feature of a preferred embodiment of the present invention, there is provided a method of obtaining data for diagnosing the condition of a living body using a UHF signal. The method includes the steps of (a) generating a UHF signal having a frequency in an ultrahigh frequency band and radiating the generated UHF signal at a first point which is one of two acupuncture points which exist on each of at least two acupuncture sections of a living body; (b) receiving a UHF signal emitted from a second point which is the other one of the two acupuncture points and detecting the magnitude of the received UHF signal; and (c) comparing the magnitude detected in step (b) with a magnitude of the UHF signal generated in step (a), calculating and recording a conductivity of each of the acupuncture sections using the result of comparison when the UHF signal passes through the corresponding acupuncture section, and obtaining at least one of a first variation and a second variation as data for diagnosing the condition of the living body, using at least two conductivities of the respective acupuncture sections, the at least two conductivities being calculated and recorded by repeatedly performing steps (a) and (b). The first variation indicates a degree of variation in conductivities of the acupuncture sections; the second variation indicates a degree of variation in conductivities for a plurality of channels.

BRIEF DESCRIPTION OF THE DRAWINGS

The above features and advantages of the present invention will become more apparent by describing in detail preferred embodiments thereof with reference to the attached drawings in which.

DETAILED DESCRIPTION OF THE INVENTION

Russian Patent Application No. 2000132892, filed on Dec. 28, 2000, and entitled: "Apparatus and Method for Obtaining Data for Diagnosing Condition of Living Body Using UHF Signal," is incorporated by reference herein in its entirety.

Hereinafter, the configuration and operations of an apparatus for obtaining data for diagnosing the condition of a living body using an ultrahigh frequency (UHF) signal according to an embodiment of the present invention and a method performed by the apparatus will be described in detail with reference to the attached drawings.

Figure 1:
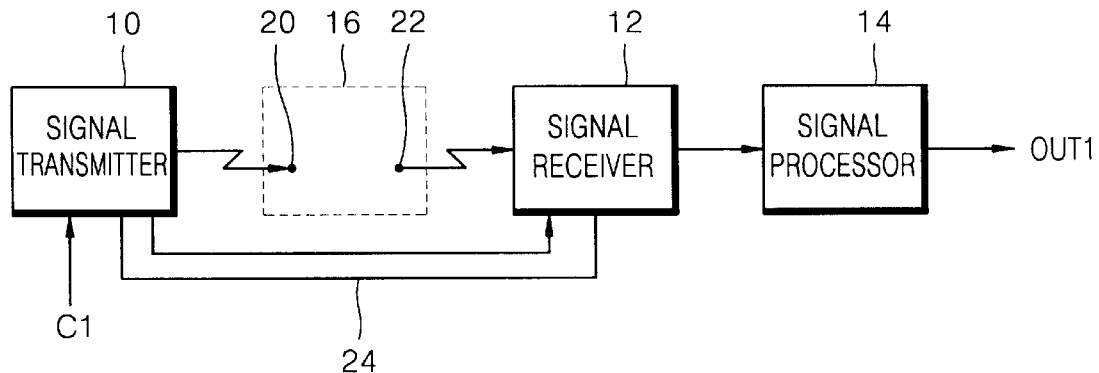
FIG. 1 illustrates a schematic block diagram of an apparatus for obtaining data for diagnosing the condition of a living body using an ultrahigh frequency (UHF) signal according to the present invention.

FIG. 1 illustrates a schematic block diagram of an apparatus for obtaining data for diagnosing the condition of a living body using a UHF signal according to an embodiment of the present invention. The apparatus includes a signal transmitter 10, a signal receiver 12, and a signal processor 14.

Figure 2:
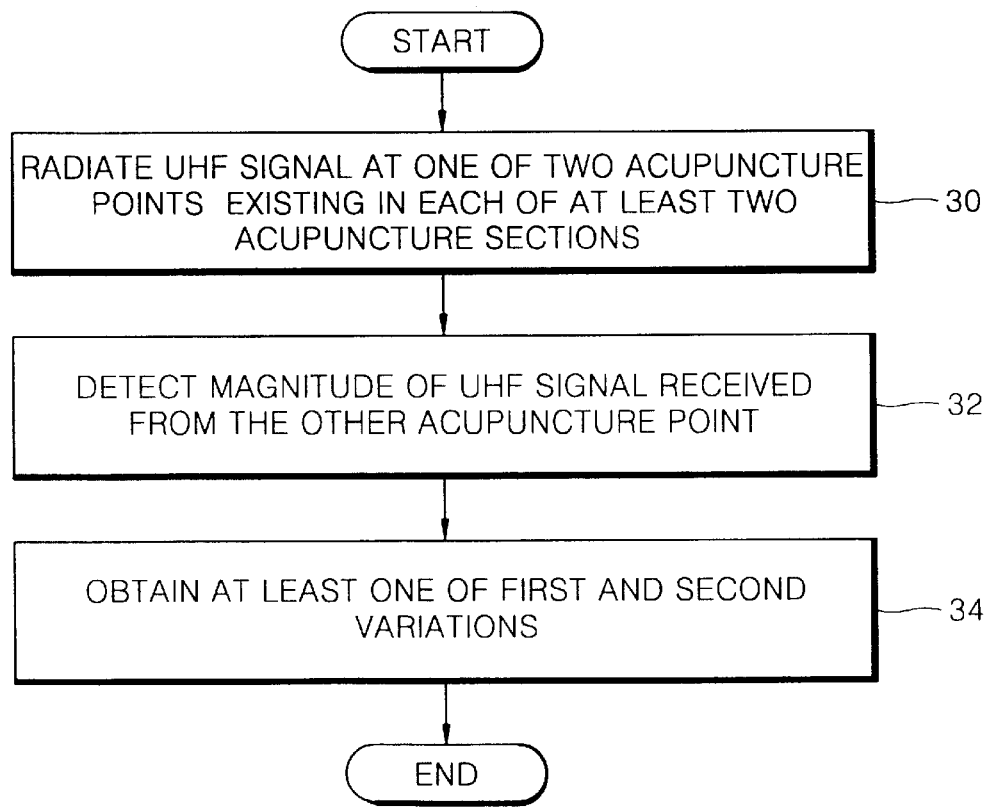
FIG. 2 illustrates a flowchart of a method of obtaining data for diagnosing the condition of a living body using a UHF signal, which is performed by the apparatus shown in FIG. 1, according to an embodiment of the present invention.

FIG. 2 illustrates a flowchart of a method of obtaining data for diagnosing the condition of a living body, which is performed by the apparatus shown in FIG. 1, according to an embodiment of the present invention. The method includes radiating and receiving a UHF signal in steps 30 and 32 and obtaining at least one of first and second variations using the magnitude of a received UHF signal in step 34.

The signal transmitter 10 shown in FIG. 1 generates a UHF signal having a frequency in a UHF band $f_s \sim f_f$ and radiates the UHF signal at a first point 20, i.e. one of two acupuncture points existing in each of at least two acupuncture sections in step 30. Here, the frequency and magnitude of the UHF signal generated by the signal transmitter 10 may be previously determined by a user or, as described later, may vary in response to a first control signal C1 received from the signal receiver 12 or the signal processor 14. The signal transmitter 10 generates a UHF signal having a minimum level and radiates it at the first point 20. The signal receiver 12 should detect the magnitude of a UHF signal received from a second point 22 when the UHF signal having the minimum level is radiated at the first point 20.

After step 30, the signal receiver 12 receives a UHF signal radiated from the second point 22, i.e. the other of the two acupuncture points, detects the magnitude of the received UHF signal, and outputs the detected magnitude to the signal processor 14 in step 32.

The first and second points 20 and 22 shown in FIG. 1 may be positioned at the same channel or different channels in a living body 16.

According to an embodiment of the present invention, at least three acupuncture points are selected starting from the end of a channel, and the adjacent first and second points 20 and 22 among the selected points may be determined as a single acupuncture section.

Figure 3:
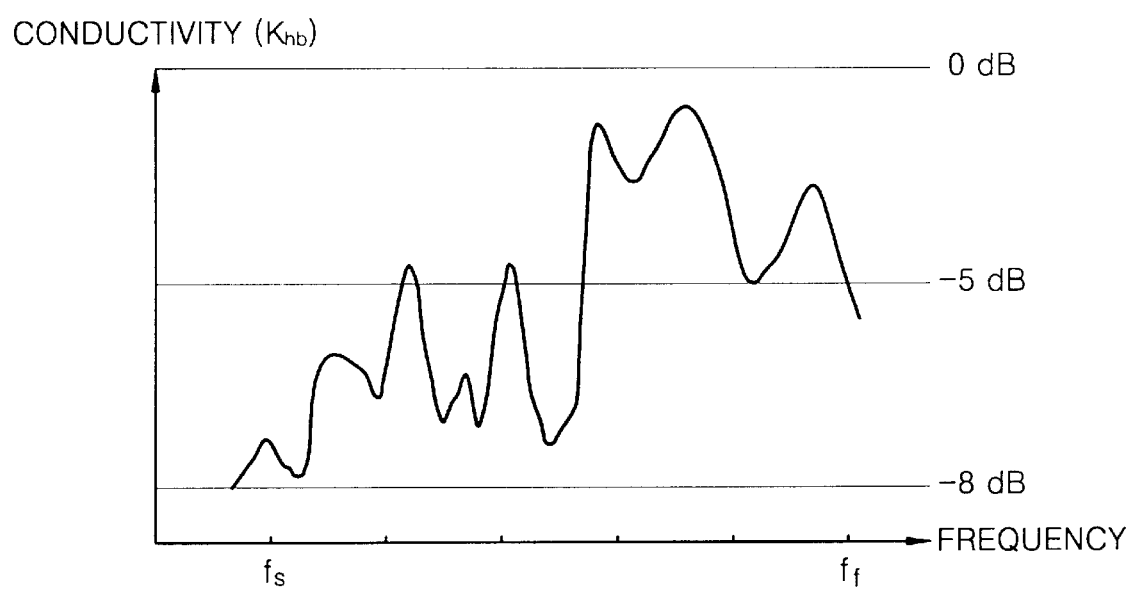
FIG. 3 illustrates a graph showing the relation between conductivity for a UHF signal and the frequency of the UHF signal in an arbitrary acupuncture section.

FIG. 3 illustrates a graph showing the relation between conductivity for a UHF signal and the frequency of the UHF signal in an arbitrary acupuncture section. Frequency is plotted on the horizontal axis, and conductivity $K_{hb}$ is plotted on the vertical axis.

Referring again to FIG. 1, after step 32, in step 34, the signal processor 14 compares the magnitude of the UHF signal received by the signal receiver 12 with the magnitude of the UHF signal generated by the signal transmitter 10, obtains and records conductivity versus frequency when the UHF signal passes through the acupuncture section based on the result of comparison, obtains at least one of first and second variations using at least two conductivities calculated and recorded for acupuncture sections after repeatedly performing steps 30 and 32, and outputs the result of calculation as data for diagnosing the condition of the living body through an output terminal OUT1. Here, the first variation indicates the degree of variation in the conductivity between acupuncture sections, and the second variation indicates the degree of variation in the conductivity between channels. Frequency versus conductivity $K_{hb}$, which is obtained by the signal processor 14 may be, for example, like the graph shown in FIG. 3.

In order to obtain the first variation, the signal processor 14 may calculate the differences in conductivity (or maximum conductivity) between acupuncture sections and determine the differences as the first variation. In order to obtain the second variation, the signal processor 14 may calculate the average of maximum conductivities for the same sections on a plurality of channels, calculate the values of deviations between the average and the maximum conductivities, and determine the deviation values as the second variation. If the first and second variations are obtained by such a procedure, the signal processor 14 may compare the first variation with a first norm obtained with respect to a healthy human body, compare the second variation with a second norm obtained with respect to a healthy human body, and determine and output at least one of the results of comparison as additional data for diagnosing the condition of a living body through the output terminal OUT1 in step 34.

For example, the signal processor 14 may compare the pattern of the first variation with the pattern of the first norm and diagnose the state of a corresponding channel from the result of comparison. Alternatively, the signal processor 14 may determine a state of a channel for which the second variation is calculated to be greater than the second norm excessive and may determine a state of a channel for which the second variation is calculated to be less than the second norm deficient. Consequently, the signal processor 14 determines the state of a channel as normal when the second variation, i.e. a value of conductivity deviation, converges on zero, and determines the state of a channel as abnormal, i.e. excessive or deficient, when the second variation goes far away from zero.

Hereinafter, the configurations and operations of preferred embodiments of an apparatus for obtaining diagnostic data shown in FIG. 1 according to an embodiment of the present invention will be described with reference to the attached drawings.

Figure 4:
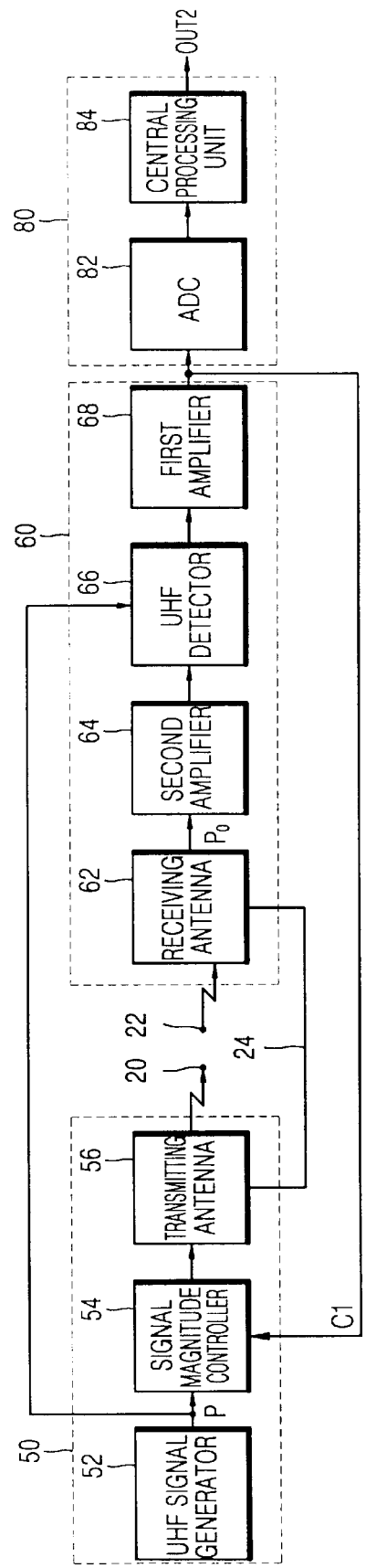
FIG. 4 illustrates a block diagram of a first preferred embodiment of the apparatus shown in FIG. 1 according to an embodiment of the present invention.

FIG. 4 illustrates a block diagram of a first preferred embodiment of the apparatus shown in FIG. 1 according to am embodiment of the present invention. The apparatus includes a signal transmitter 50, a signal receiver 60, and a signal processor 80.

To perform step 30, the signal transmitter 50 shown in FIG. 4 may include a UHF signal generator 52, a signal magnitude controller 54, and a transmitting antenna 56. The UHF signal generator 52 generates a UHF signal having a predetermined frequency and a predetermined magnitude and outputs the generated UHF signal to the signal magnitude controller 54. Then, the signal magnitude controller 54 controls the magnitude of the UHF signal in response to a first control signal C1 received from the signal receiver 60 and outputs the UHF signal having a controlled magnitude to the transmitting antenna 56. Here, the first control signal C1 indicates a magnitude detected from a received UHF signal. As shown in FIG. 4, the first control signal C1 may indicate the magnitude of a UHF signal received by the signal receiver 60. The signal receiver 60 detects the magnitude of the received UHF signal. The transmitting antenna 56 radiates the UHF signal having the magnitude controlled by the signal magnitude controller 54 at a first point 20.

To perform step 32, the signal receiver 60 may include a receiving antenna 62, first and second amplifiers 68 and 64, and a UHF detector 66. The receiving antenna 62 receives a UHF signal emitted from a second point 22 and outputs the received UHF signal to the second amplifier 64. Then, the second amplifier 64 amplifies the UHF signal received through the receiving antenna 62 while removing noise, that is, the second amplifier 64 amplifies a noise component less than a signal component. The second amplifier 64 outputs the result of amplification to the UHF detector 66. According to an embodiment of the present invention, the second amplifier 64 may have a noise factor of 2.5 dB or less. The UHF detector 66 detects the magnitude of the received UHF signal from the result of the amplification received from the second amplifier 64 and outputs the detected magnitude to the first amplifier 68.

According to an embodiment of the present invention, unlike FIG. 4, the signal receiver 60 may not include the second amplifier 64. In this case, the receiving antenna 62 outputs the received UHF signal to the UHF detector 66, and the UHF detector 66 detects the magnitude of the UHF signal received through the receiving antenna 62 and outputs the detected magnitude to the first amplifier 68.

According to one embodiment of the present invention, as shown in FIG. 4, the UHF detector 66 can detect the magnitude of the UHF signal received from the receiving antenna 62 or the second amplifier 64 in synchronization with the UHF signal generated by the UHF signal generator 52. In other words, the UHF detector 66 can detect the magnitude of a received UHF signal whenever the UHF signal generator 52 generates a UHF signal.

According to another embodiment of the present invention, unlike FIG. 4, the UHF detector 66 can detect the magnitude of the received UHF signal without receiving the UHF signal generated by the UHF signal generator 52.

The first amplifier 68 amplifies the magnitude received from the UHF detector 66 and outputs the amplified magnitude as the detected magnitude of the received UHF signal to the signal processor 80.

To perform step 34, the signal processor 80 may include an analog-to-digital converter (ADC) 82 and a central processing unit 84. The ADC 82 converts the analog magnitude received from the signal receiver 60 into a digital magnitude and outputs the digital magnitude to the central processing unit 84. Then, the central processing unit 84 calculates the conductivity of the UHF signal from the digital magnitude received from the ADC 82, calculates at least one of first and second variations, and outputs the result of calculation as diagnostic data through an output terminal OUT2. Here, the central processing unit 84 may be installed within a personal computer (not shown), or both the central processing unit 84 and the ADC 82 may be installed within the personal computer.

Figure 5:
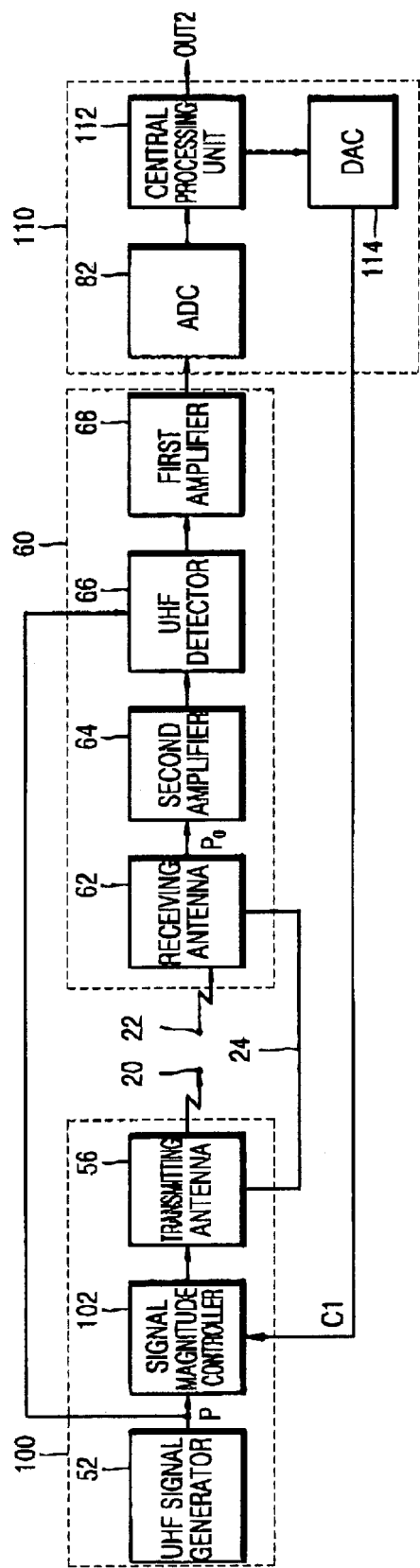
FIG. 5 illustrates a block diagram of a second preferred embodiment of the apparatus shown in FIG. 1 according to an embodiment of the present invention.

FIG. 5 illustrates a block diagram of a second preferred embodiment of the apparatus shown in FIG. 1 according to an embodiment of the present invention. In the second embodiment, the apparatus includes a signal transmitter 100, a signal receiver 60, and a signal processor 110.

The signal transmitter 100, the signal receiver 60, and the signal processor 110 shown in FIG. 5 perform the same functions as the signal transmitter 50, the signal receiver 60, and the signal processor 80 shown in FIG. 4. In addition, the signal transmitter 100 and the signal receiver 60 of FIG. 5 have the same configurations as the signal transmitter 50 and the signal receiver 60 of FIG. 4. Thus, descriptions of the same parts will not be repeated.

Unlike the signal magnitude controller 54 shown in FIG. 4, a signal magnitude controller 102 of the signal transmitter 100 shown in FIG. 5 receives a first control signal C1 from the signal processor 110 instead of the signal receiver 60. For this, a central processing unit 112, unlike the central processing unit 84 shown in FIG. 4, generates the first control signal C1 in a digital form using a conductivity obtained from the magnitude of a received UHF signal. The magnitude of the received UHF signal is received from the ADC 82. Here, unlike the signal processor 80 shown in FIG. 4, the signal processor 110 further includes a digital-to-analog converter (DAC) 114 for converting the first control signal C1 received from the central processing unit 112 from digital form into analog form and outputting the first control signal C1 in analog form to the signal magnitude controller 102.

Here, the apparatus for obtaining data for diagnosing the condition of a living body shown in FIG. 5 can detect the magnitude of a received UHF signal in synchronization with a UHF signal generated by a UHF signal generator 52 using amplitude modulation. For example, the central processing unit 112 outputs a trigger signal for synchronization in digital form to the DAC 114. Then, the DAC 114 converts the trigger signal from digital form into analog form and outputs the trigger signal in analog form to the signal magnitude controller 102 together with the first control signal C1. Then, the signal magnitude controller 102 controls the magnitude of a UHF signal in response to the first control signal C1, embeds the trigger signal in the UHF signal having the controlled magnitude, and outputs the UHF signal containing the trigger signal to the signal receiver 60 through the transmitting antenna 56. Accordingly, the UHF detector 66 of the signal receiver 60 can detect the magnitude of a received UHF signal in synchronization with the UHF signal generated by the UHF signal generator 52 using the trigger signal contained in the received UHF signal.

Figure 6:
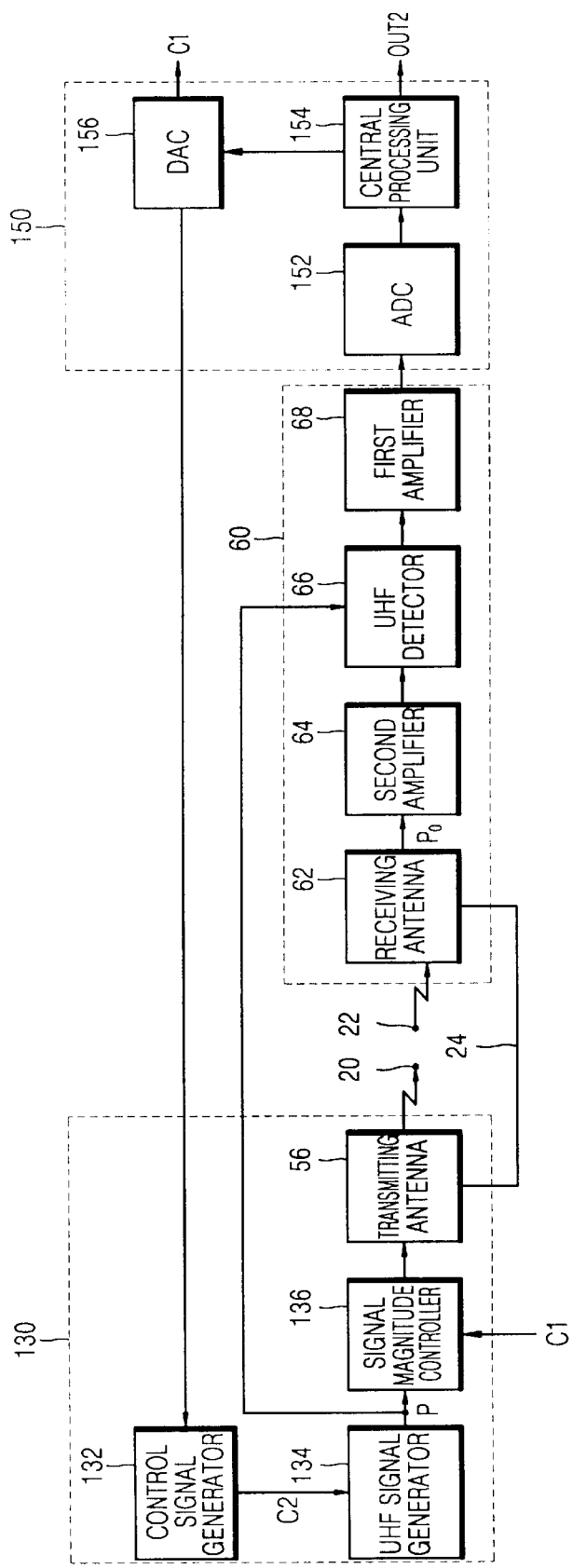
FIG. 6 illustrates a block diagram of a third preferred embodiment of the apparatus shown in FIG. 1 according to an embodiment of the present invention.

FIG. 6 illustrates a block diagram of a third preferred embodiment of the apparatus shown in FIG. 1 according to an embodiment of the present invention. In the third embodiment, the apparatus includes a signal transmitter 130, a signal receiver 60, and a signal processor 150.

The signal transmitter 130, the signal receiver 60, and the signal processor 150 shown in FIG. 6 perform the same functions as the signal transmitter 50, the signal receiver 60, and the signal processor 80 shown in FIG. 4. In addition, the signal receiver 60 of FIG. 6 has the same configuration as the signal receiver 60 of FIG. 4. Thus, descriptions of the same part will not be repeated.

Unlike the signal transmitter 50 shown in FIG. 4, the signal transmitter 130 shown in FIG. 6 further includes a control signal generator 132 for generating a second control signal C2 in response to information data received from the signal processor 150 and outputting the second control signal C2 to a UHF signal generator 134. For this, according to a program, a central processing unit 154 of the signal processor 150 determines a frequency and a magnitude of a UHF signal to be generated by a UHF signal generator 134 and outputs the determined frequency and magnitude as information data in digital form. Here, the signal processor 150 further includes a DAC 156 for converting the information data received from the central processing unit 154 from digital form into analog form and outputs the analog information data to the control signal generator 132.

Unlike the UHF signal generator 52 shown in FIG. 4, the UHF signal generator 134 shown in FIG. 6 generates a UHF signal having at least one of the determined magnitude and the determined frequency in response to the second control signal C2 received from the control signal generator 132 and outputs the generated UHF signal to a signal magnitude controller 136.

Figure 7:
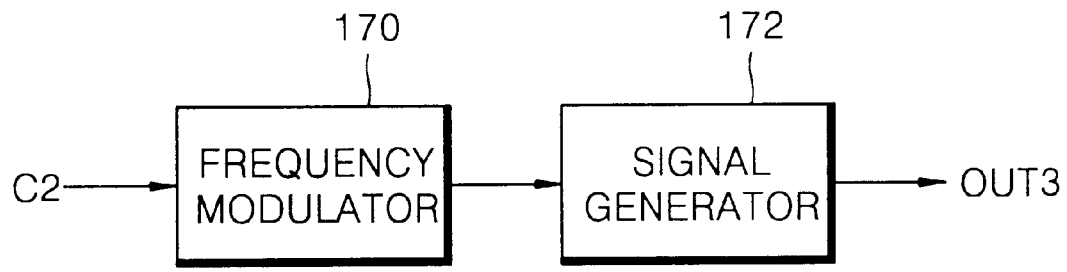
FIG. 7 illustrates a block diagram of a preferred embodiment of a UHF signal generator shown in FIG. 6 according to an embodiment of the present invention.

FIG. 7 illustrates a block diagram of a preferred embodiment of the UHF signal generator 134 shown in FIG. 6 according to an embodiment of the present invention. The UHF signal generator 134 includes a frequency modulator 170 and a signal generator 172.

In FIG. 7, the frequency modulator 170 modulates a frequency in response to the second control signal C2 received from the control signal generator 132 and outputs the modulated frequency to the signal generator 172. Then, the signal generator 172 determines a magnitude of a UHF signal according to the modulated frequency received from the frequency modulator 170, generates a UHF signal having the determined magnitude and the modulated frequency, and outputs the generated UHF signal through an output terminal OUT3 to the signal magnitude controller 136.

The signal magnitude controller 136 of the signal transmitter 130 shown in FIG. 6 performs the same function as the signal magnitude controller 54 or 102 shown in FIG. 4 or 5. For example, the signal magnitude controller 136 may receive the first control signal C1 from the signal transmitter 60, as shown in FIG. 4, or from the DCA 156 of the signal processor 150, as shown in FIG. 6. For example, in the case where the first control signal C1 is received from the signal processor 150, like the central processing unit 112 shown in FIG. 5, the central processing unit 154 shown in FIG. 6 generates the first control signal C1 in digital form using a conductivity obtained from the magnitude of a received UHF signal, which is received from an ADC 152, and outputs the first control signal C1 to the DAC 156. Then, like the DAC 114 shown in FIG. 5, the DAC 156 converts the first control signal C1 received from the central processing unit 154 from digital form into analog form and outputs the first control signal C1 in analog form to the signal magnitude controller 136.

Hereinafter, in FIGS. 4 through 6 showing embodiments of an apparatus for obtaining data for diagnosing the condition of a living body according to an embodiment of the present invention, the relations among a conductivity $K_{hb}$ for a UHF signal passing through a living body, a UHF signal P generated by the UHF signal generator 52 or 134, and a UHF signal $P_0$ received through the receiving antenna 62 will be described.

A conductivity $K_{hb}$ of a section between the first and second points 20 and 22 on the skin and its variation) $K_{hb}$ are influenced by the electrical characteristics of the tissue, the structure of the subcutaneous tissue, the distance between the first and second points 20 and 22, a measured frequency, a measuring time, the number of measurements, etc., and they vary with the state of a channel. When it is assumed that the amplification factor of the second amplifier 64 is $K_p$, that the volt-watt sensitivity of the UHF detector 66 is $K_d$, that a magnitude detected by the UHF detector 66 is U, and that the amplification factor of the first amplifier 68 is $K_u$, the output $U_u$ of the first amplifier 68 is expressed by Formula (1).

$$U_u = UK_u \quad (1)$$

Here, when it is assumed that a maximum output of the signal magnitude controller 54, 102, or 136 is $U_m$, the amplification factor $K_t$ of the signal magnitude controller 54, 102, or 136 is expressed by Formula (2).

$$K_t = (1 - U_u/U_m) \quad (2)$$

Since a change in the variation) $K_{hb}$ is reflected to the signal transmitter 50, 100, or 130 through negative feedback from the signal receiver 60 or the signal processor 80, 110, or 150 to the signal transmitter 50, 100, or 130, the magnitude of a UHF signal transmitted from the transmitting antenna 56 can be automatically controlled by the signal magnitude controller 54, 102, or 136. Here, if an apparatus for obtaining diagnostic data according to the present invention, which includes the feedback loop, is realized as a two-terminal network, the amplification factor, that is, the transfer function $K_0$, of the two-terminal network is expressed by Formula (3).

$$K_0 = P_0/P = K_{hb}/(1 + K_{hb}K_r) \quad (3)$$

Here, $K_r$ is transmission gain for a negative feedback loop and is expressed by Formula (4).

$$K_r = K_t K_a K_p K_d K_u \quad (4)$$

Here, $K_a$ indicates the conductivity of the transmitting or receiving antenna 56 or 62. The output U of the UHF detector 66 can be expressed by Formula (5).

$$U = K_p K_d P_0 \quad (5)$$

In Formula (3), since $K_{hb}K_r$ is at least 100 and $K_r >> K_{hb}$, $K_0$ decreases by a factor of $(1 + K_{hb}K_r)$.

First, in the case where as the transmitting and receiving antennas 56 and 62 are positioned on a copperplate, the conductivity $K_{hb1}$ for a UHF signal has a maximum value 1, the transfer function $K_{01}$ of the two-terminal network is expressed by Formula (6).

$$K_{01} = K_{hb1}/(1 + K_{hb1}K_r) = 1/(1 + K_r) \quad (6)$$

Here, since $K_r >> K_{hb1}$, $K_{01}$ becomes $K_r^{-1}$. For example, $K_{01}$ can be $10^{-6}$, and the amplification factor $K_{t1}$ of the signal magnitude controller 54, 102, or 136 is expressed by Formula (7).

$$K_{t1} = (1 - U_{u1}/U_m) \quad (7)$$

When the second amplifier 64 sees the UHF signal generated by the UHF signal generator 52 or 134, under the condition that a signal-to-noise ratio (SNR) exceeds 10, a minimum level $P_{min}$ of a signal which can be detected by the receiving antenna 62 is expressed by Formula (8).

$$P_{min} = F_n kT)f \quad (8)$$

Here, $F_n$ indicates the noise factor of the second amplifier 64, k indicates a Boltzmann's constant, T indicates absolute temperature, and) f indicates the frequency bandwidth of the second amplifier 64.

For example, when $F_n = 1.12$,)$f = 430$ MHz, and T=300 EK, the minimum level $P_{min}$ is $2 \text{H} 10^{-12}$ W. Accordingly, an input $P_0$ of the second amplifier 64 can decrease as shown in Formula (9).

$$P_0 \exists 2 \text{H} 10^{-11} \text{W} \quad (9)$$

Consequently, since $P_0$ can be decreased, the magnitude of the UHF signal generated by the UHF signal generator 52 or 134 can be decreased. Therefore, bodily harm that may be caused by irradiation by a high power UHF signal may be avoided. In addition, the signal receiver 60 has good sensitivity, being able to detect a UHF signal having a small magnitude. Accordingly, errors occurring due to poor sensitivity of the signal receiver 60 when conductivity is measured may be reduced.

Next, when the transmitting and receiving antennas 56 and 62 are respectively positioned at the first and second points 20 and 22 on the skin, and the conductivity $K_{hb2}$ for a UHF signal has a minimum value $10^{-4}$, if $K_r$ is $10^6$, the transfer function $K_{02}$ of an apparatus according to an embodiment of the present invention is expressed by Formula (10).

$$K_{02} = K_{hb2}/(1 + K_{hb2}K_r) = 10^{-4}/(1 + 10^{-4} 10^6) = 10^{-6} \quad (10)$$

Accordingly, the amplification factor $K_{t2}$ of the signal magnitude controller 54, 102, or 136 is expressed by Formula (11).

$$K_{t2} = (1 - U_{u2}/U_m) \quad (11)$$

Consequently, when it is assumed that the amplification factors of the signal magnitude controller 54, 102, or 136 are $K_{t1}$ and $K_{t2}$, respectively, at the maximum value $K_{hb1}$ and the minimum value $K_{hb2}$ of the conductivity $K_{hb}$, power and an amplification factor $K_r$ needed by the UHF signal generator 52 or 134 can be determined using $K_{t1}$ and $K_{t2}$.

Meanwhile, according to an embodiment of the present invention, the sensitivity of the signal receiver 60 may be increased by setting the frequency bandwidth) f of the second amplifier 64, which is expressed in Formula (8), to be small.

Hereinafter, the configurations and operations of embodiments of the transmitting antenna 56 of the signal transmitter 10, 50, 100, or 130 and the receiving antenna 62 of the signal receiver 12 or 60 shown in FIGS. 1 and 4 through 6 according to an embodiment of the present invention will be described with reference to the attached drawings.

Figure 8:
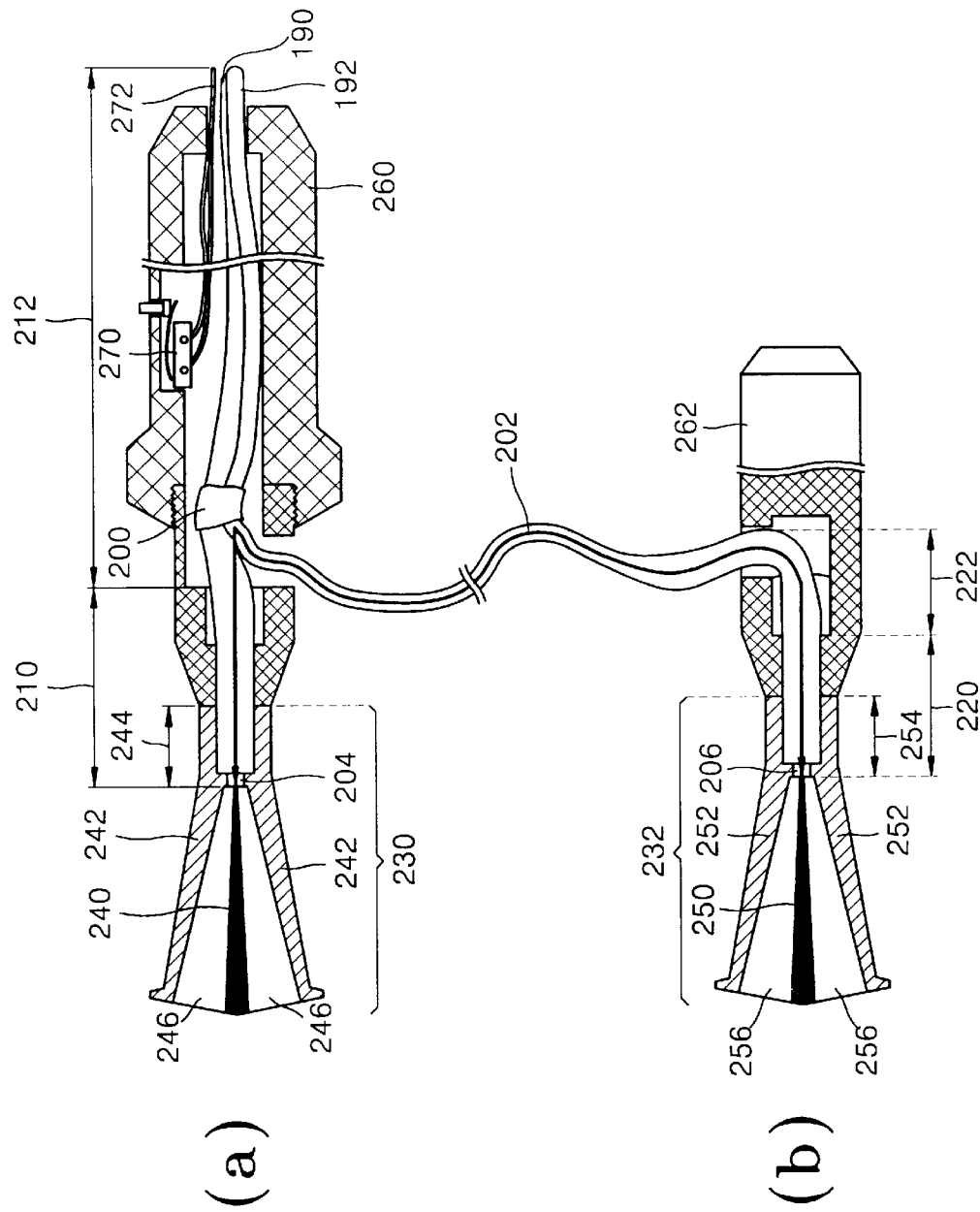
FIG. 8 illustrates a schematic diagram of a firs t preferred embodiment of a transmitting antenna and a receiving antenna according to an embodiment of the present invention.

FIG. 8 illustrates a schematic diagram of a first preferred embodiment of the transmitting antenna 56 and the receiving antenna 62 according to an embodiment of the present invention. In FIG. 8, (a) may denote the transmitting antenna 56 and (b) may denote the receiving antenna 62, or (a) may denote the receiving antenna 62 and (b) may denote the transmitting antenna 56. Hereinafter, it is assumed that (a) denotes the transmitting antenna 56 and (b) denotes the receiving antenna 62.

According to a preferred embodiment of the present invention, the transmitting and receiving antennas 56 and 62 shown in (a) and (b) of FIG. 8 include coaxial cables 190 and 192 fixed by insulator handles 260 and 262.

The coaxial cables 190 and 192 are electrically connected at a contact portion 200. As shown in (a) of FIG. 8, the coaxial cables 190 and 192 are guided together from the outside of the transmitting antenna 56 to the electrical contact portion 200 through the handle 260 and diverge at the electrical contact portion 200. One of the coaxial cables 190 and 192 is guided to the receiving antenna 62 shown in (b) of FIG. 8.

In FIGS. 1 and 4 through 6, reference numeral 24 denotes an electrical connection. Here, the electrical contact portion 200 may be positioned at the transmitting antenna 56, as shown (a) of FIG. 8, or may be positioned at the receiving antenna 62, unlike (a) of FIG. 8.

According to an embodiment of the present invention, the length of a section 202 between an end 204 of the transmitting antenna 56 shown in (a) of FIG. 8, which contacts the first point 20, and an end 206 of the receiving antenna 62, which contacts the second point 22, is controlled not to exceed ¾ of a minimum wavelength in a UHF band $f_s$–$f_f$ of a UHF signal generated by the signal transmitter 10, 50, 100, or 130. This is for minimizing influence exerted on the conductivity $K_a$ of each of the transmitting and receiving antennas 56 and 62 according to the mutual position between the transmitting antenna 56 and the receiving antenna 62.

Each of the coaxial cables 190 and 192 has a flexible portion and an inflexible portion. For example, the transmitting antenna 56 shown in (a) of FIG. 8 has an inflexible portion 210 and a flexible portion 212. The receiving antenna 62 shown in (b) of FIG. 8 has an inflexible portion 220 and a flexible portion 222.

According to an embodiment of the present invention, the transmitting antenna 56 shown in (a) of FIG. 8 may further include an impedance matching unit 230 in order to reduce the attenuation of a UHF signal radiated from the transmitting antenna 56 to the first point 20. Then, even if the magnitude of a UHF signal radiated from the transmitting antenna 56 is attenuated, the UHF detector 66 can detect the magnitude of a received UHF signal. Here, the impedance matching unit 230 is provided between the end 204 of an internal wire of the coaxial cable 190 and the first point 20, and performs a function of matching the impedance of the end 204 with the impedance of the first point 20, that is, a function of reducing a difference in impedance between the first point 20 and the transmitting antenna 56. For this, the impedance matching unit 230 includes an external wire 240 extending from the end 204 of the internal wire to the first point 20 and a shielding member 242 for integrally shielding an end portion 244 of the transmitting antenna 56 and the external wire 240.

Similarly, as shown in (b) of FIG. 8, the receiving antenna 62 may further include an impedance matching unit 232 in order to reduce the attenuation of a UHF signal received from the second point 22 through the receiving antenna 62. Here, the impedance matching unit 232 is provided between the end 206 of an internal wire of the coaxial cable 192 and the second point 22 and performs a function of matching the impedance of the end 206 with the impedance of the second point 22, that is, a function of reducing a difference in impedance between the second point 22 and the receiving antenna 62. For this, the impedance matching unit 232 includes an external wire 250 extending from the end 206 of the internal wire to the second point 22 and a shielding member 252 for integrally shielding an end portion 254 of the receiving antenna 62 and the external wire 250.

According to an embodiment of the present invention, in each of the impedance matching units 230 and 232 shown in FIG. 8, a space 246 or 256 surrounding the external wire 240 or 250 within the shielding member 242 or 252 can be filled with air or an insulator. In addition, a signal input switch 270 shown in (a) of FIG. 8 is provided at the insulator handle 260 and performs a function of connecting user information, which is input through a signal cable 272 guided from the outside, to the central processing unit 84, 112, or 154.

Figure 9:
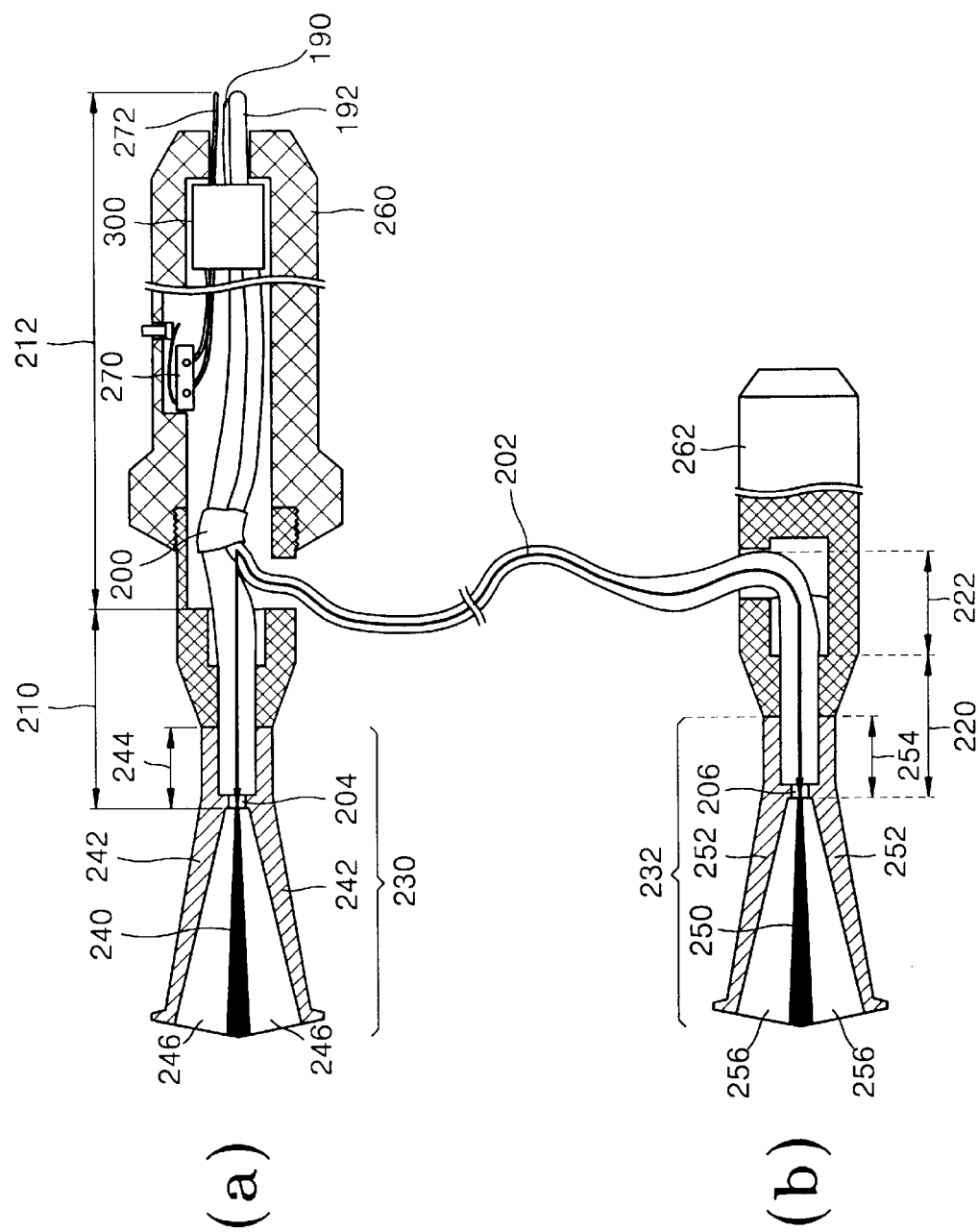
FIG. 9 illustrates a schematic diagram of a second preferred embodiment of a transmitting antenna and a receiving antenna according to an embodiment of the present invention.

FIG. 9 illustrates a schematic diagram of a second preferred embodiment of the transmitting antenna 56 and the receiving antenna 62 according to an embodiment of the present invention. In FIG. 9, (a) may denote the transmitting antenna 56 and (b) may denote the receiving antenna 62, or (a) may denote the receiving antenna 62 and (b) may denote the transmitting antenna 56.

Unlike the transmitting antenna 56 shown in (a) of FIG. 8, the transmitting antenna 56 shown in (a) of FIG. 9 may include at least one (300) among the UHF signal generator 52 or 134, the signal magnitude controller 54, 102, or 136, the control signal generator 132, and the signal processor 80, 110, or 150 shown in FIG. 4, 5, or 6. Alternatively, unlike the receiving antenna 62 shown in (b) of FIG. 8, the receiving antenna 62 shown in (a) of FIG. 9 may include at least one (300) among the UHF detector 66, the first and second amplifiers 68 and 64, and the signal processor 80, 110, or 150 shown in FIG. 4, 5, or 6.

Figure 10:
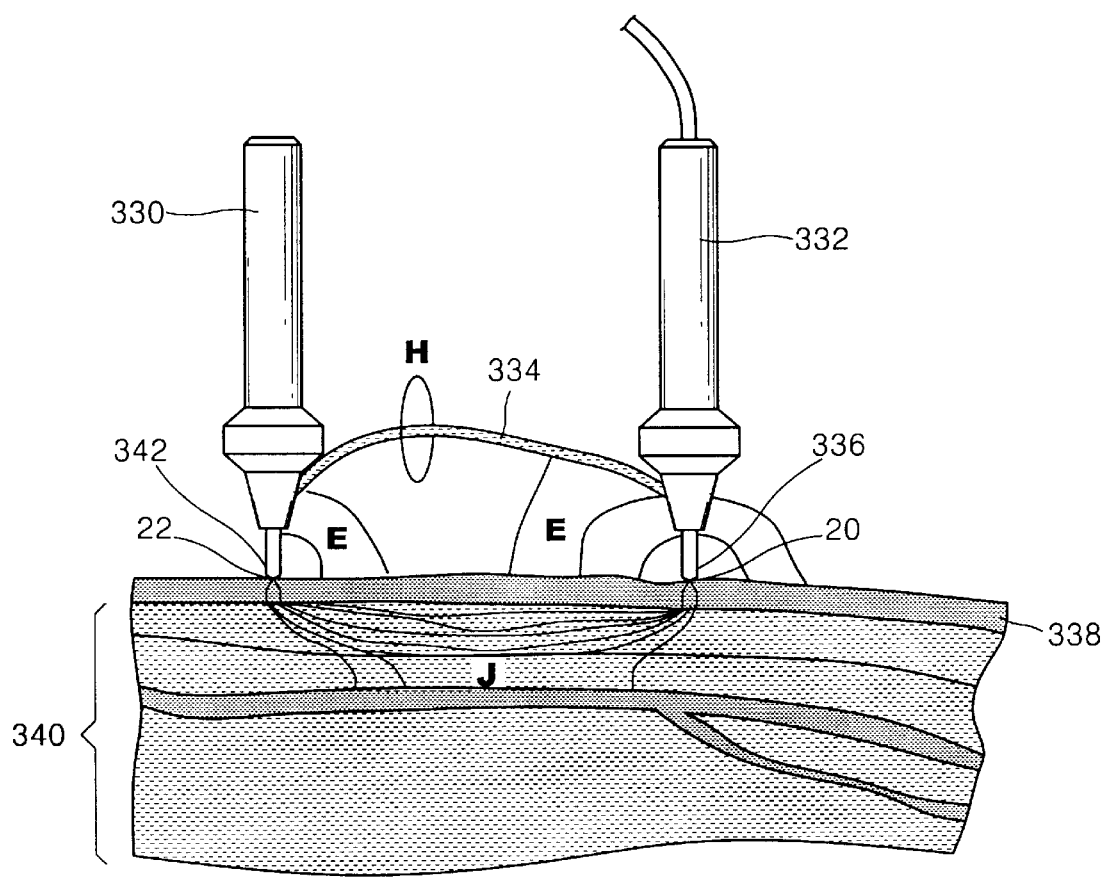
FIG. 10 illustrates a diagram showing a state in which a transmitting antenna and a receiving antenna contact a first point and a second point, respectively.

FIG. 10 illustrates a diagram showing a state in which the transmitting antenna 56 and the receiving antenna 62 contact the first point 20 and the second point 22, respectively.

Hereinafter, it is assumed that reference numeral 330 denotes the receiving antenna 62 and reference numeral 332 denotes a transmitting antenna 56.

As shown in FIG. 10, when an end 336 of the transmitting antenna 332 contacts the first point 20 on skin 338, a current density J (a bold letter indicates a vector) is induced through a subcutaneous tissue 340 and electric fields E are formed on the skin 338 and in space. Here, the current density J is proportional to the conductivity of the subcutaneous tissue 340. An electric field E and a magnetic field H are formed at a cable 334 connecting the transmitting antenna 332 to the receiving antenna 330. Here, an end 342 of the receiving antenna 330 contacts the second point 22 on the skin 338 and receives a UHF signal.

When a UHF signal is radiated at the skin 338, the transmitting antenna 332 is managed to vertically contact the first point 20 so that an internal wire in an end portion 336 of the transmitting antenna 332 can completely contact the first point 20 on the skin 338. Similarly, when a UHF signal is received from the skin 338, the receiving antenna 330 is managed to vertically contact the second point 22 so that an internal wire in an end portion 342 of the receiving antenna 330 can completely contact the second point 22 on the skin 338.

Hereinafter, under the assumption that a living body is a human body, cases of applying an apparatus for obtaining diagnostic data, its embodiments, and a method thereof to a human body and cases of diagnosing the condition of a patient using the obtained diagnostic data will be described with reference to the attached drawings.

First, the following is an excerpt from a record of a patient's condition.

The patient complained of a headache associated with a high blood pressure (250/140), cardiac pain associated with physical strain, breathlessness due to fatigue, dry mouth, thirst, and loss of 7 kg weight per year. The patient has been troubled with dry mouth and thirst for the last two years. The glycemia was 7 mMol/l two weeks ago. However, the health condition of the patient has not taken a turn for the better. The patient has had hypertension over 20 years, and his blood pressure has increased to at least 190 mmHg over the last five years. A physical examination has shown that the patient's heartbeat is rhythmical and slow, pulse rate is 78 beats/min, and blood pressure is 180/105 mmHg. In conclusion, the condition of the patient is diagnosed as diabetes with complications, i.e., secondary hypertension, third composite obesity, ischemia, and secondary cardiagra.

In order to obtain diagnostic data for this patient, four acupuncture points Jing1, Ying, Yu, and Jing2 are set starting from an end of each of 12 channels. The 12 channels are the large intestine channel LI, the triple warmer channel TW, the small intestine channel SI, the heart channel H, the pericardium channel PC, the lung channel Lu, the spleen channel Sp, the liver channel Liv, the stomach channel St, the gallbladder channel GB, the bladder channel UB, and the kidney channel K.

To obtain the conductivity of a first acupuncture section Jing1-Ying on a first channel among the 12 channels, a UHF signal generated from the UHF signal generator 52 or 134 of the signal transmitter 10, 50, 100, or 130 is controlled to have a minimum level by the signal magnitude controller 54, 102, or 136 and is radiated through the transmitting antenna 56 at the first point Jing1. Then, the signal receiver 12 or 60 receives the UHF signal from the second point Ying, detects the magnitude of the received UHF signal, and outputs the detected magnitude to the signal processor 14, 80, 110, or 150. The central processing unit 84, 112, or 154 of the signal processor 14, 80, 110, or 150, as described above, obtains and records a maximum value of the conductivity of the first acupuncture section Jing1-Ying on the first channel. In the same manner, maximum values of conductivities of the second acupuncture section Ying-Yu and third acupuncture section Yu-Jing2 on the first channel are obtained. Then, in the same manner, maximum values of conductivities of first through third acupuncture sections on each of the second through twelfth channels are obtained. Here, it is assumed that maximum values of the conductivities of the first through third acupuncture sections on the first through twelfth channels are obtained as shown Table 1.

TABLE 1

|  | LI | TW | SI | H | PC | Lu | Sp | Liv | St | GB | UB | K |
| --- | --- | --- | --- | --- | --- | --- | --- | --- | --- | --- | --- | --- |
| Jing1-Ying | 469 | 530 | 420 | 167 | 481 | 615 | 1050 | 603 | 527 | 604 | 605 | 604 |
| Ying-Yu | 560 | 605 | 453 | 241 | 135 | 690 | 830 | 654 | 645 | 658 | 645 | 548 |
| Yu-Jing2 | 670 | 645 | 530 | 436 | 132 | 453 | 126 | 750 | 760 | 754 | 754 | 421 |

Here, the average of the maximum values of the conductivity for each acupuncture section on the first through twelfth channels is obtained and is replaced by 0 dB. For each acupuncture section, a deviation between a maximum value and an average, that is, a conductivity deviation which is the second variation is calculated using Formula (12), with respect to 0 dB.

$$\text{Conductivity deviation} = 20\log(\text{maximum value/average}) \quad (12)$$

Figure 11:
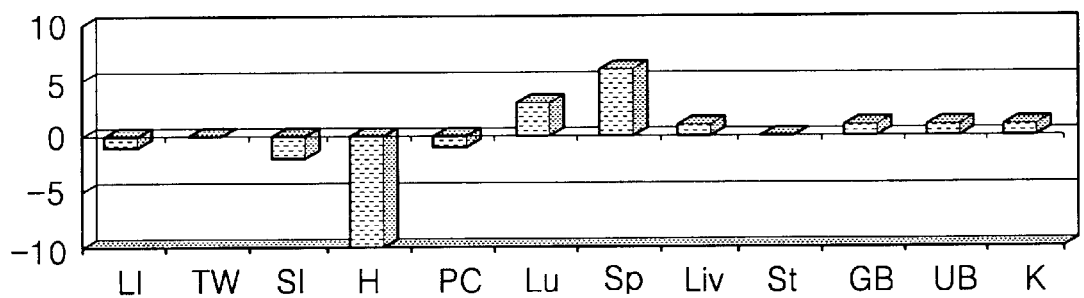
FIG. 11 illustrates a graph showing the values of conductivity deviation for a first acupuncture section at first through twelfth channels.

FIG. 11 illustrates a graph of conductivity deviations for the first acupuncture section at the first through twelfth channels. The channels are shown on the horizontal axis, and conductivity deviations are measured along the vertical axis.

For example, conductivity deviations for the first acupuncture sections Jing1-Ying at the first through twelfth channels may be obtained as shown in Table 2 and FIG. 11.

TABLE 2

| LI | TW | SI | H | PC | Lu | Sp | Liv | St | GB | UB | K |
|---|---|---|---|---|---|---|---|---|---|---|---|
| −1 | 0 | −2 | −10 | −1 | 1 | 6 | 1 | 0 | 1 | 1 | 1 |

Here, "−" indicates that the value is smaller than 0 dB, "+" indicates that the value is greater than 0 dB.

For example, when the second norm ranges from −5 to +5, referring to FIG. 11, the signal processor 14, 80, 110, or 150 determines that the heart channel H beyond the range of the second norm for a normal person is in a deficient state and the spleen channel Sp is in an excessive state. Therefore, by comparing the second variation with the second norm obtained according to the present invention, it is possible to accurately determine that there is a deficient state of the heart channel H, as is mentioned in the record of the patient's condition.

For a more accurate diagnosis, the signal processor 14, 80, 110, or 150 may inspect the degree of variation, that is, the first variation, in maximum values of the conductivities of the first through third acupuncture sections Jing1-Ying, Ying-Yu, and Yu-Jing2 at each channel.

Figure 12:
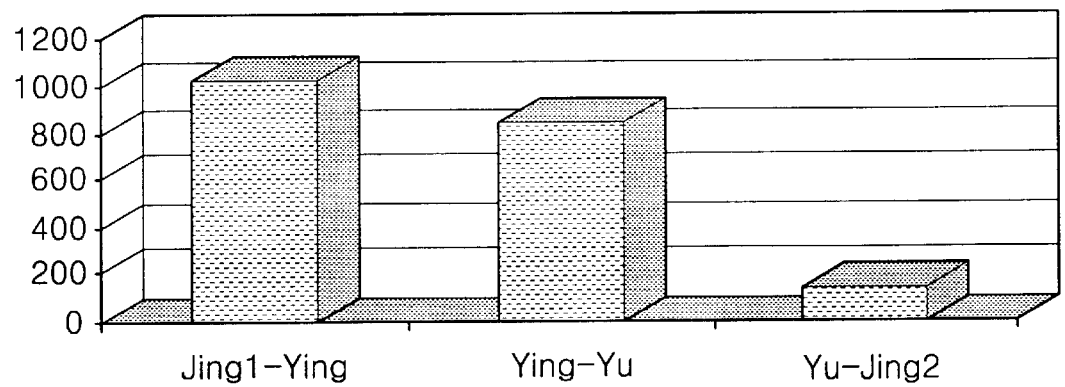
FIG. 12 illustrates a graph showing a first variation with respect to a spleen channel.
Figure 13:
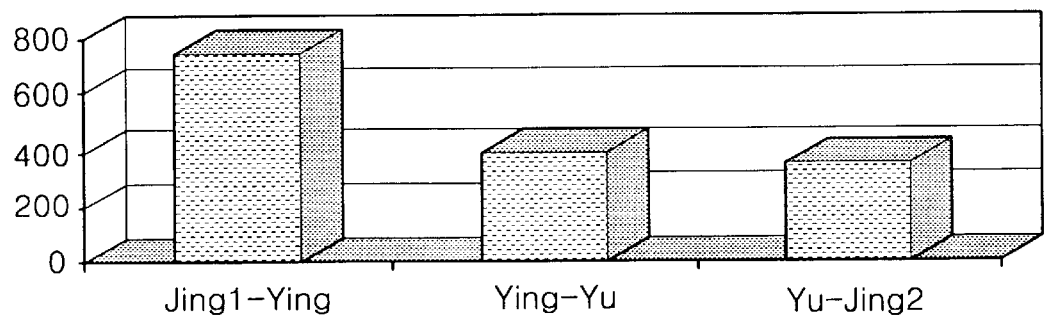
FIG. 13 illustrates a graph showing a first norm with respect to a spleen channel.

FIG. 12 illustrates a graph of the first variation with respect to the spleen channel Sp. The acupuncture sections are shown on the horizontal axis, and maximum values of the conductivities are measured along the vertical axis. FIG. 13 illustrates a graph of the first norm with respect to the spleen channel Sp. The acupuncture sections are shown on the horizontal axis, and maximum values of the conductivities are measured along the vertical axis.

For example, maximum values of the conductivities of the first through third acupuncture sections Jing1-Ying, Ying-Yu, and Yu-Jing2 at the spleen channel Sp may be extracted from Table 1 as shown in Table 3 and FIG. 12.

TABLE 3

|  | Jing1-Ying | Ying-Yu | Yu-Jing2 |
|---|---|---|---|
| Sp | 1050 | 830 | 126 |

Generally, the first variation indicating the degree of variation in maximum values of the conductivities of acupuncture sections at each channel is peculiar to each channel. When the first norm for a normal person is as shown in Table 4 and FIG. 13, the signal processor 14, 80, 110, or 150 compares the graph shown in FIG. 12 and the graph shown in FIG. 13, and can indirectly estimate the relationship between the state of the spleen channel Sp and diabetes according to the characteristics of the distribution of maximum values of the conductivities of the acupuncture sections at the spleen channel Sp.

TABLE 4

|  | Jing1-Ying | Ying-Yu | Yu-Jing2 |
|---|---|---|---|
| Sp | 759 | 401 | 350 |

Figure 14:
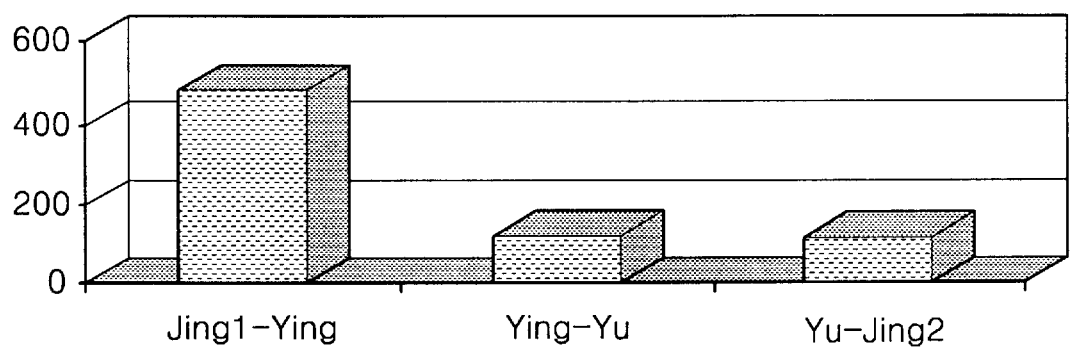
FIG. 14 illustrates a graph showing a first variation with respect to a pericardium channel.
Figure 15:
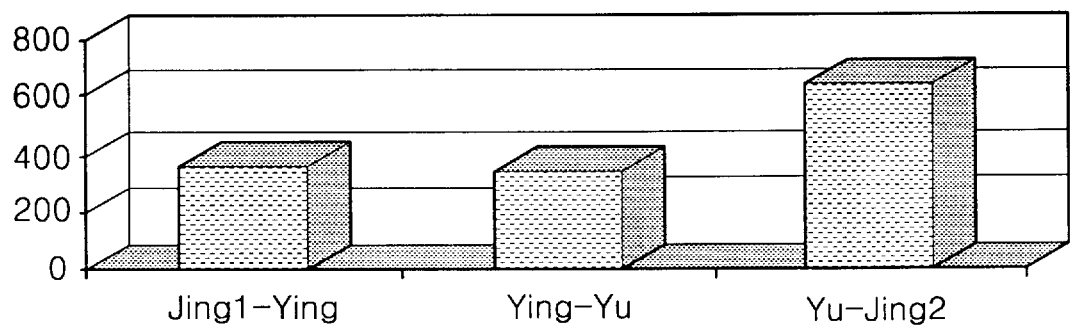
FIG. 15 illustrates a graph showing a first norm with respect to a pericardium channel.

FIG. 14 illustrates a graph of the first variation with respect to the pericardium channel PC. The acupuncture sections are shown on the horizontal axis, and maximum values of the conductivities are measured along the vertical axis. FIG. 15 illustrates a graph of the first norm with respect to the pericardium channel PC. The acupuncture sections are shown on the horizontal axis, and maximum values of the conductivities are measured along the vertical axis.

As shown in FIG. 11, the conductivity deviation for the first acupuncture section Jing1-Ying at the pericardium channel PC is within the range (−5 through +5) of the second norm. However, when the first variation perceived from the distribution of maximum values of conductivities of the first through third acupuncture sections Jing1-Ying, Ying-Yu, and Yu-Jing2 at the pericardium channel PC shown in FIG. 14 is compared with the first norm for a normal person shown in FIG. 15, it may be found that there is a difference. Accordingly, it may be determined that there is a chronic disorder in energy circulation in the pericardium channel PC based on diagnostic data output from the signal processor 14, 80, 110, or 150 corresponding to the result of comparing the first variation and the first norm. Consequently, it may be determined that the patient has a complication such as hypertension, as described in the above record of the patient's condition.

Second, the following is an excerpt from a record of another patient's condition. When examined, the patient had chronic cholesystitis at moderate exacerbation and hepatitis as a complication. In addition, the patient had urolithiasis and a small calculus in an upper capsule of the left kidney as other complications. Urine examination indicated a leukocyte count of 2–4. Ultrasound investigation of the abdominal cavity indicated that the patient had chronic stone-free cholesystitis, urolithiasis (small clod of sand in the pelvis of the right kidney and a calculus having a size of 5 mm in the upper capsule of the left kidney), and malformation of the liver and the pancreas.

In order to obtain diagnostic data for this patient, four acupuncture points Jing1, Ying, Yu, and Jing2 are set starting from an end of each of 12 channels. To obtain the conductivity of a first acupuncture section Jing1-Ying on a first channel among the 12 channels, a UHF signal generated from the UHF signal generator 52 or 134 of the signal transmitter 10, 50, 100, or 130 is controlled to have a minimum level by the signal magnitude controller 54, 102, or 136 and is radiated through the transmitting antenna 56 at the first point Jing1. Then, the signal receiver 12 or 60 receives the UHF signal from the second point Ying, detects the magnitude of the received UHF signal, and outputs the detected magnitude to the signal processor 14, 80, 110, or 150. The central processing unit 84, 112, or 154 of the signal processor 14, 80, 110, or 150, as described above, obtains and records a maximum value of the conductivity of the first acupuncture section Jing1-Ying on the first channel. In the same manner, maximum values of the conductivities of the second acupuncture section Ying-Yu and the third acupuncture section Yu-Jing2 on the first channel are obtained. In the same manner, maximum values of conductivities of first through third acupuncture sections on each of the second through twelfth channels are obtained. Here, it is assumed that maximum values of the conductivities of the first through third acupuncture sections on the first through twelfth channels are obtained as shown in Table 5.

TABLE 5

|  | LI | TW | SI | H | PC | Lu | Sp | Liv | St | GB | UB | K |
|---|---|---|---|---|---|---|---|---|---|---|---|---|
| Jing1-Ying | 165 | 303 | 240 | 251 | 238 | 249 | 529 | 544 | 336 | 835 | 1005 | 127 |
| Ying-Yu | 327 | 328 | 230 | 250 | 345 | 353 | 128 | 144 | 350 | 438 | 986 | 150 |
| Yu-Jing2 | 198 | 439 | 249 | 378 | 460 | 169 | 116 | 139 | 432 | 169 | 890 | 65 |

Here, the average of the maximum values of the conductivity for each acupuncture section on the first through twelfth channels is obtained and is replaced by 0 dB. For each acupuncture section, a deviation between a maximum value and an average, that is, a conductivity deviation which is the second variation is calculated using Formula (12) with respect to 0 dB.

Figure 16:
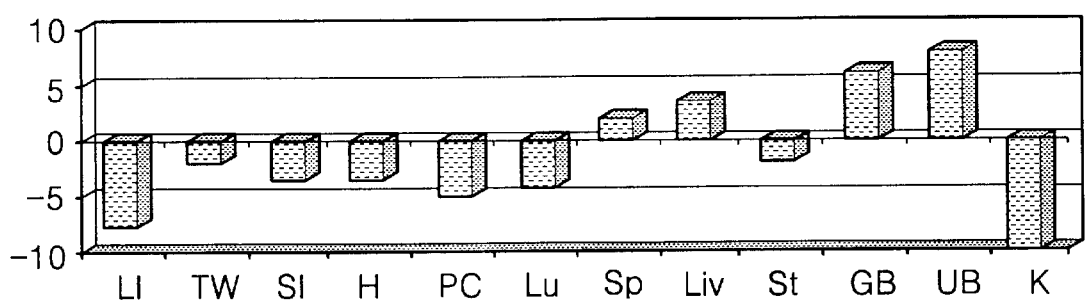
FIG. 16 illustrates another graph showing the values of conductivity deviation for the first acupuncture section at the first through twelfth channels.

FIG. 16 illustrates another graph of conductivity deviations of the first acupuncture sections at the first through twelfth channels. The channels are shown on the horizontal axis, and conductivity deviations are measured along the vertical axis.

For example, conductivity deviations for the first acupuncture sections Jing1-Ying at the first through twelfth channels may be obtained as shown in Table 6 and FIG. 16.

TABLE 6

| LI | TW | SI | H | PC | Lu | Sp | Liv | St | GB | UB | K |
|---|---|---|---|---|---|---|---|---|---|---|---|
| −8 | −2 | −4 | −4 | −5 | −4 | 2 | 3 | −2 | 6 | 8 | −10 |

For example, when the second norm ranges from −5 to +5, referring to Table 6 and FIG. 16, the signal processor 14, 80, 110, or 150 determines that the large intestine channel LI and the kidney channel K beyond the range of the second norm for a normal person are in a deficient state and the gallbladder channel GB and the bladder channel UB are in an excessive state. Therefore, by using diagnostic data corresponding to a result of comparing the second variation with the second norm obtained according to the present invention, it is possible to accurately determine, as is mentioned in the record of the patient's condition, that there is a disorder in kidney function due to calculi in the kidneys caused by the excessive state of the bladder channel UB.

For a more accurate diagnosis, the signal processor 14, 80, 110, or 150 may inspect the degree of variation, that is, the first variation, in maximum values of the conductivities of the first through third acupuncture sections Jing1-Ying, Ying-Yu, and Yu-Jing2 at each channel.

Figure 17:
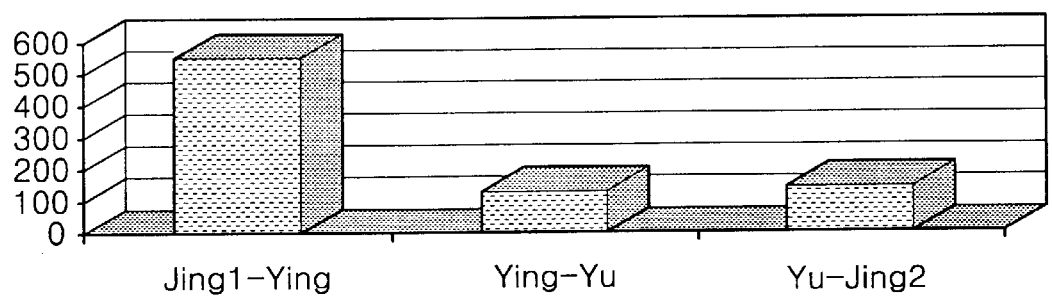
FIG. 17 illustrates a graph showing a first variation with respect to a liver channel.
Figure 18:
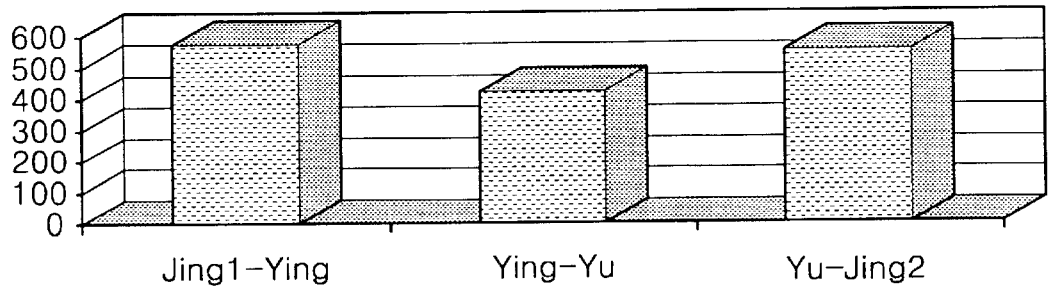
FIG. 18 illustrates a graph showing a first norm with respect to a liver channel.

FIG. 17 illustrates a graph of the first variation with respect to the liver channel Liv. The acupuncture sections are shown on the horizontal axis, and maximum values of the conductivities are measured along the vertical axis. FIG. 18 illustrates a graph of the first norm with respect to the liver channel Liv. The acupuncture sections are shown on the horizontal axis, and maximum values of the conductivities are measured along the vertical axis.

For example, maximum values of the conductivities of the first through third acupuncture sections Jing1-Ying, Ying-Yu, and Yu-Jing2 at the liver channel Liv may be extracted from Table 5 as shown in Table 7 and FIG. 17.

TABLE 7

|  | Jing1-Ying | Ying-Yu | Yu-Jing2 |
|---|---|---|---|
| Liv | 544 | 144 | 139 |

When the first norm for a normal person is as shown in Table 8 and FIG. 18, the signal processor 14, 80, 110, or 150 compares the graph shown in FIG. 17 and the graph shown in FIG. 18 and can indirectly estimate the relationship between the state of the liver channel Liv and diabetes according to the characteristics of the distribution of maximum values of conductivities at the liver channel Liv.

TABLE 8

|  | Jing1-Ying | Ying-Yu | Yu-Jing2 |
|---|---|---|---|
| Liv | 579 | 414 | 550 |

For example, the conductivity deviation for the first acupuncture section Jing1-Ying at the liver channel Liv is within the normal range (−5 through +5) of the second norm, as shown in FIG. 16. However, when the first variation perceived from the distribution of maximum values of conductivities of the first through third acupuncture sections Jing1-Ying, Ying-Yu, and Yu-Jing2 at the liver channel Liv shown in FIG. 17 is compared with the first norm for a normal person shown in FIG. 18, a difference may be seen. Accordingly, it may be determined that there is a chronic disorder in energy circulation in the liver channel Liv based on diagnostic data output from the signal processor 14, 80, 110, or 150 corresponding to the result of comparing the first variation and the first norm. Consequently, it may be determined that the patient has a complication such as hepatitis, as described in the above record of the patient's condition.

As described above, an apparatus and method for obtaining data for diagnosing the condition of a living body using a UHF signal according to the present invention may provide sufficient data for diagnosing the condition of a living body, thereby allowing the condition of the living body to be accurately diagnosed. In addition, since the present invention can lower the level of a UHF signal radiated at a living body, harm to living tissue may be avoided.

A preferred embodiment of the present invention has been disclosed herein and, although specific terms are employed, they are used in a generic and descriptive sense only and not for purpose of limitation. Accordingly. It will be readily apparent to those of ordinary skill in the art that various changes in form and details may be made without departing from the spirit and scope of the invention as set forth in the following claims.

What is claimed is:

1. An apparatus for obtaining data for diagnosing the condition of a living body using an ultrahigh frequency (UHF) signal, the apparatus comprising:

a signal transmitter for generating a UHF signal having a frequency in an ultrahigh frequency band and radiating the generated UHF signal at a first point which is one of two acupuncture points which exist on each of at least two acupuncture sections of a living body, said sections being located on one or more acupuncture channels, a signal receiver for receiving a UHF signal emitted from a second point which is the other one of the two acupuncture points, detecting the magnitude of the received UHF signal, and outputting the detected magnitude; and a signal processor for comparing the detected magnitude of the received UHF signal with a magnitude of the UHF signal generated by the signal transmitter, calculating from the result of comparison and recording a conductivity of each of the acupuncture sections when the UHF signal passes through the corresponding acupuncture section, calculating at least one of a first variation, which indicates a degree of variation in conductivities of the acupuncture sections, and a second variation, which indicates a degree of variation in conductivities for a plurality of said acupuncture channels, using at least two recorded conductivities of the respective acupuncture sections, and outputting the result of calculation as data for diagnosing the condition of the living body.

2. The apparatus of claim 1, wherein the signal processor compares a first norm for a normal person with the first variation, compares a second norm for a normal person with the second variation, and determines at least one of the results of comparison as another data for diagnosing the condition of the living body.

3. The apparatus of claim 1, wherein the signal transmitter generates the UHF signal having a minimum level, and when the UHF signal having the minimum level is radiated at the first point, the signal receiver detects the magnitude of the UHF signal received from the second point.

4. The apparatus of claim 1, wherein the signal transmitter comprises:

a UHF signal generator for generating the UHF signal and outputting the generated UHF signal;

a signal magnitude controller for controlling the magnitude of the UHF signal in response to a first control signal and outputting the UHF signal having the controlled magnitude, the first control signal being determined according to the magnitude detected from the received UHF signal; and a transmitting antenna for radiating the UHF signal having the controlled magnitude at the first point.

5. The apparatus of claim 4, wherein the signal transmitter further comprises a control signal generator for generating a second control signal in response to information data received from the signal processor, and the UHF signal generator generates the UHF signal having at least one of a magnitude and a frequency which are determined in response to the second control signal.

6. The apparatus of claim 5, wherein the UHF signal generator comprises:

a frequency modulator for modulating a frequency in response to the second control signal and outputting the modulated frequency; and a signal generator for generating the UHF signal having the modulated frequency and a magnitude determined corresponding to the modulated frequency and outputting the generated UHF signal to the signal magnitude controller.

7. The apparatus of claim 5, wherein at least one among the UHF signal generator, the signal magnitude controller, the control signal generator, and the signal processor is installed within the transmitting antenna.

8. The apparatus of claim 1, wherein the signal receiver comprises:

a receiving antenna for receiving the UHF signal emitted from the second point;

a UHF detector for detecting the magnitude of the UHF signal received through the receiving antenna and outputting the detected magnitude; and a first amplifier for amplifying the magnitude received from the UHF detector and outputting the result of amplification as the magnitude detected from the received UHF signal to the signal processor.

9. The apparatus of claim 8, wherein the signal transmitter comprises:

a UHF signal generator for generating and outputting the UHF signal;

a signal magnitude controller for controlling the magnitude of the UHF signal in response to a first control signal and outputting the UHF signal having the controlled magnitude, the first control signal being determined according to the detected magnitude of the received UHF signal; and a transmitting antenna for radiating the UHF signal having the controlled magnitude at the first point.

10. The apparatus of claim 8, wherein the signal receiver further comprises a second amplifier for amplifying the received UHF signal while removing noise and outputting the result of amplification to the UHF detector, and the UHF detector detects the magnitude from the result of amplification received from the second amplifier and outputs the detected magnitude to the first amplifier.

11. The apparatus of claim 8, wherein at least one among the UHF detector, the first amplifier, and the signal processor is installed within the receiving antenna.

12. The apparatus of claim 10, wherein the second amplifier is installed within the receiving antenna.

13. The apparatus of claim 10, wherein a frequency bandwidth of the second amplifier is set to be small.

14. The apparatus of claim 10, wherein a noise factor of the second amplifier is no greater than 2.5 dB.

15. The apparatus of claim 9, wherein the result of amplification from the first amplifier is output as the first control signal to the signal magnitude controller.

16. The apparatus of claim 9, wherein the UHF detector detects the magnitude of the received UHF signal in synchronization with the UHF signal generated by the UHF signal generator.

17. The apparatus of claim 8, wherein the signal processor comprises:

an analog-to-digital converter for converting the detected magnitude received from the signal receiver into digital form; and a central processing unit for calculating the conductivity using the magnitude received in the digital form from the analog-to-digital converter and calculating at least one of the first and second variations.

18. The apparatus of claim 9, wherein the signal processor comprises:
   an analog-to-digital converter for converting the detected magnitude received from the signal receiver into digital form; and
   a central processing unit for calculating the conductivity using the magnitude received in the digital form from the analog-to-digital converter and calculating at least one of the first and second variations.

19. The apparatus of claim 18, wherein the signal processor further comprises a digital-to-analog converter for converting the first control signal from digital form into analog form and outputting the first control signal in analog form to the signal magnitude controller.

20. The apparatus of claim 18, wherein the signal transmitter further comprises a control signal generator for generating a second control signal based on information data received from the signal processor, and the UHF signal generator generates the UHF signal having at least one of a magnitude and a frequency which are determined in response to the second control signal.

21. The apparatus of claim 20, wherein the signal processor further comprises a digital-to-analog converter for converting the information data received from the central processing unit from a digital form into an analog form and outputting the analog information data to the control signal generator.

22. The apparatus of claim 21, wherein the signal receiver generates the first control signal and outputs the generated first control signal to the signal magnitude controller.

23. The apparatus of claim 21, wherein the digital-to-analog converter converts the first control signal from digital form into analog form and outputs the first control signal in analog form to the signal magnitude controller.

24. The apparatus of claim 17, wherein the central processing unit is installed within a personal computer.

25. The apparatus of claim 17, wherein the analog-to-digital converter and the central processing unit are installed within a personal computer.

26. The apparatus of claim 9, wherein the transmitting antenna and the receiving antenna comprise coaxial cables, respectively, and the coaxial cables are electrically connected.

27. The apparatus of claim 26, wherein the coaxial cables are electrically connected in the transmitting antenna.

28. The apparatus of claim 26, wherein the coaxial cables are electrically connected in the receiving antenna.

29. The apparatus of claim 26, wherein a length of a section between an end of the transmitting antenna, the end contacting the first point, and an end of the receiving antenna, the end contacting the second point, does not exceed ¾ of a minimum wavelength of the UHF signal, which is generated by the signal transmitter, in a UHF band.

30. The apparatus of claim 26, wherein each of the coaxial cables comprises a flexible portion and an inflexible portion.

31. The apparatus of claim 26, wherein at least one of the transmitting antenna and the receiving antenna comprises an impedance matching unit, which is provided between an end of an internal wire within the coaxial cable and the first or second point, for matching an impedance of the end of the internal wire with an impedance of the first or second point.

32. The apparatus of claim 31, wherein the impedance matching unit comprises:
   an external wire extending from the end of the internal wire to the first or second point; and
   a shielding member for integrally shielding an end portion of the transmitting or receiving antenna and the external wire.

33. The apparatus of claim 32, wherein an inner space surrounding the external wire in the shielding member is filled with air.

34. The apparatus of claim 32, wherein an inner space surrounding the external wire in the shielding member is filled with a dielectric.

35. A method of obtaining data for diagnosing the condition of a living body using an ultrahigh frequency (UHF) signal, the method comprising the steps of:
   (a) generating a UHF signal having a frequency in an ultrahigh frequency band and radiating the generated UHF signal at a first point which is one of two acupuncture points which exist on each of at least two acupuncture sections of a living body, said sections being located on one or more acupuncture channels,
   (b) receiving a UHF signal emitted from a second point which is the other one of the two acupuncture points and detecting the magnitude of the received UHF signal; and
   (c) comparing the magnitude detected in step (b) with a magnitude of the UHF signal generated in step (a), calculating and recording a conductivity of each of the acupuncture sections using the result of comparison when the UHF signal passes through the corresponding acupuncture section, and obtaining at least one of a first variation and a second variation as data for diagnosing the condition of the living body, using at least two conductivities of the respective acupuncture sections, the at least two conductivities being calculated and recorded by repeatedly performing steps (a) and (b), the first variation indicating a degree of variation in conductivities of the acupuncture sections, the second variation indicating a degree of variation in conductivities for a plurality of said acupuncture channels.

36. The method of claim 35, wherein the step (c) comprises comparing a first norm for a normal person with the first variation, comparing a second norm for a normal person with the second variation, and determining at least one of the results of comparison as another data for diagnosing the condition of the living body.

37. The method of claim 36, wherein a state of a channel for which the second variation is greater than the second norm is determined excessive, and a state of a channel for which the second variation is less than the second norm is determined deficient.

38. The method of claim 35, wherein at least three acupuncture points are selected starting from an end of each channel, and a section between adjacent acupuncture points among the selected acupuncture points is determined as an acupuncture section.

39. The method of claim 35, wherein the step (c) comprises calculating differences between conductivities of the acupuncture sections and determining the calculated differences as the first variation.

40. The method of claim 35, wherein the step (c) comprises:
   calculating an average of maximum values of the conductivities of the same acupuncture sections existing on the plurality of channels; and
   calculating deviations between the average and the maximum values and determining the calculated deviations as the second variation.

41. The method of claim 35, wherein the first and second points are on the same channel.

42. The method of claim 35, wherein the first and second points are on different channels.

* * * * *